United States Patent [19]

Murtha

[11] Patent Number: 4,520,129

[45] Date of Patent: May 28, 1985

[54] HYDROGENATION CATALYST

[76] Inventor: Timothy P. Murtha, c/o Phillips Petroleum Company, Bartlesville, Okla. 74004

[21] Appl. No.: 496,783

[22] Filed: May 20, 1983

Related U.S. Application Data

[62] Division of Ser. No. 293,068, Aug. 17, 1981, Pat. No. 4,409,401.

[51] Int. Cl.³ .......................... B01J 27/02; B01J 31/02; B01J 27/20
[52] U.S. Cl. .................................... 502/222; 502/168; 502/174; 502/216; 502/223
[58] Field of Search ............... 502/168, 216, 174, 222, 502/223

[56] References Cited

U.S. PATENT DOCUMENTS

| | | | |
|---|---|---|---|
| 2,559,325 | 7/1948 | Spillane et al. | 502/216 |
| 3,076,810 | 2/1963 | Duggan et al. | 260/586 |
| 3,366,684 | 1/1968 | Budd | 260/576 |
| 3,592,758 | 7/1971 | Inwood | 208/89 |
| 3,636,027 | 1/1972 | Smith | 260/453 PC |
| 3,872,028 | 3/1975 | Pijnter et al. | 252/439 |
| 3,947,495 | 3/1976 | Murib et al. | 252/428 |
| 3,959,382 | 5/1976 | Yeh et al. | 260/586 |
| 3,974,096 | 8/1976 | Segura et al. | 252/439 |
| 4,010,214 | 3/1977 | Gelfand | 252/429 A' |
| 4,043,942 | 8/1977 | Wilson, Jr. | 252/430 |
| 4,064,154 | 12/1977 | Chandra et al. | 252/428 |
| 4,117,099 | 9/1978 | Merkl | 502/222 X |
| 4,148,758 | 4/1979 | Eberly | 252/436 |
| 4,162,267 | 7/1979 | Fisher et al. | 260/586 P |
| 4,164,515 | 8/1979 | Van Peppen et al. | 260/586 |
| 4,169,587 | 10/1979 | Murtha | 260/586 P |
| 4,199,522 | 4/1980 | Murchison et al. | 502/222 X |
| 4,200,553 | 4/1980 | Van Peppen et al. | 252/447 |
| 4,203,923 | 5/1980 | Yeh et al. | 568/362 |
| 4,242,234 | 12/1980 | Schlinger et al. | 502/222 |
| 4,356,316 | 10/1982 | Aoshima et al. | 252/439 |

FOREIGN PATENT DOCUMENTS 2909783  9/1980  Fed. Rep. of Germany .

OTHER PUBLICATIONS

Paul N. Rylander, "Catalytic Hydrogenation Over Platinum Metals", (1967), pp. 16–22.
Morris Freifelder, *Practical Catalytic Hydrogenation*, 9/7/71, pp. 35–53.
Carleton Ellis, *Hydrogenation of Organic Substances*, 3rd edition, (1930), pp. 41 and 42.

*Primary Examiner*—William G. Wright

[57] ABSTRACT

The reduction of organic compounds is made more selective by modifying the reduction catalysts with compounds of sulfur.

10 Claims, No Drawings

HYDROGENATION CATALYST

This application is a divisional application of copending application Ser. No. 293,068 filed Aug. 17, 1981 now U.S. Pat. No. 4,409,401.

BACKGROUND

Organic hydrogenation reactions are often of low yield when a specific product is desired. Attempts to increase the specificity, i.e., the proportion of a particular reaction product, have involved changes in various reaction conditions.

Applicant has discovered that sulfur, which is normally considered a poison for hydrogenation catalysts, can be used to increase the selectivity of certain hydrogenation reactions.

THE INVENTION

The catalytic hydrogenation of phenol to cyclohexanone using a sodium-promoted palladium catalyst is improved by contacting the catalyst with at least one sulfur-containing compound.

OBJECTS OF THE INVENTION

It is an object of the invention to improve the selectivity of certain hydrogenation catalysts.

It is another object of the invention to increase the quantity of alicyclic ketone product which is derived from the hydrogenation of an aromatic hydroxy compound.

It is a further object of the invention to increase the amount of cyclohexanone produced via the hydrogenation of phenol using a palladium metal catalyst.

DESCRIPTION OF THE INVENTION

The Organic Feed

The feedstock is selected from the class of compounds which are monocyclic aromatic compounds having hydroxyl substituents. Alkyl substituents having 1–6 carbon atoms per alkyl group can be present. The total number of carbon atoms in the alkyl substituents can range from 1–12 carbon atoms per molecule. Examples of suitable feedstock compounds include phenol, 2-methylphenol, 4-methylphenol; 2,4-dimethylphenol; 2,4,6-trimethylphenol; 4-tert-butylphenol; 2-methyl-4-tert-butylphenol; 4-hexylphenol; 2-methyl-4-hexyl-6-pentylphenol; 3,5-dihexylphenol; 3-methylphenol and mixtures thereof. Phenol is the preferred feedstock.

THE CATALYST

The catalysts of the invention contain palladium. The palladium is present in the catalyst at concentrations of 0.01–5 wt. % based on the total catalyst weight. Preferably, the catalysts contain 0.1–1.0 wt. % metal.

The catalyst of the invention will preferably contain a carrier for the metal component. Suitable carriers include silica-alumina, silica, and alumina. Alumina is preferred.

The effectiveness of the palladium catalyst employed is enhanced by the inclusion of an alkaline promoter. Useful alkaline promoters are well known. They include alkali metals and compounds thereof. Sodium carbonate is a preferred promoter. The alkaline promoter, when used, is present in a concentration lying between 0.1 and 5 wt. %, based on a total catalyst weight.

It is also desirable, when a continuous hydrogenation process is employed, to add small quantities of an alkaline compound with the feedstock, e.g. preferably from 1 to about 10 ppm based on the weight of the feedstock. Sodium compounds such as sodium hydroxide or sodium carbonate can be employed in this manner.

TREATMENT OF THE CATALYST

The catalyst of the invention is obtained by incorporating sulfur in the catalyst. The catalyst can be thus modified with sulfur by incorporating an inorganic sulfur compound in the catalyst preparation stage or by adding an organic sulfur compound with the feed during the startup of the hydrogenation reaction or preferably by a combination of these two methods.

It is highly preferred to heat the sulfided catalyst (obtained by a combination of the sulfiding methods described above) in the presence of an oxidizing gas and subsequently in the presence of a reducing gas. While air is the preferred, other useful oxidizing gases are oxygen and oxygen/inert gas mixtures. Useful reducing gases, with hydrogen preferred, are light hydrocarbons/hydrogen mixtures.

When air and hydrogen are employed, the heating in air is conducted at 150°–250° C. for 1–4 hours while the heating in the presence of hydrogen is conducted at 150°–250° C. for 4–12 hours. It should be noted that these times and temperatures are not critical. In general, any parameters which favor effective oxidation and subsequent reduction are useful herein.

In one embodiment, a sodium-promoted palladium-alumina catalyst was impregnated with sodium sulfide. The resultant catalyst was used to reduce phenol to cyclohexanone at a 97% conversion rate and 60% selectivity.

In another embodiment, the sodium sulfide-treated catalyst above was further modified with a small amount of thioanisole in the phenol feed and heated in air to 180°–233° C. then in hydrogen at 212° C. This catalyst gave a conversion of over 94% and a cyclohexanone selectivity of 94%.

The use of a soluble sulfur-containing agent in the feedstream is advantageous because the catalyst can be modified in place in the reaction zone to increase its selectivity to the desired product. After treatment with the sulfur-containing agent in the feedstream, fresh feed, containing no added sulfur, can be reintroduced for further reaction.

The sulfur compounds used to treat the catalysts of the invention are organic or inorganic in character. Generally, they are compounds of divalent sulfur, i.e. substances in which the sulfur present has a valence of 2. Tri-, quadri-, and hexa-valent sulfur materials are operable, but are less preferred.

Useful organic compounds of divalent sulfur include sulfides, disulfides, thioacids and mercaptans (thiols). Cyclic and acyclic organic sulfur compounds are suitable. Examples of suitable compounds include di-n-butyl sulfide, diethyl disulfide, cyclohexanethiol, 1-octanethiol, butanedithioic acid and ethanethioic acid. Thiophene and thioanisole are preferred.

Useful inorganic sulfur compounds include sulfides and hydrosulfides. Sulfur compounds containing alkali and/or alkaline earth metals are preferred. Examples of suitable compounds include potassium sulfide, lithium sulfide, calcium sulfide, calcium hydrosulfide, sodium hydrosulfide and potassium hydrosulfide. Sodium sulfide is highly preferred.

Combinations of one or more organic sulfur compounds with one or more inorganic sulfur compounds are contemplated for use in the treatment operations.

The amount of sulfur compound to be added is such that the sulfur content of the final catalyst will range from 0.001 to 1 wt. %, based on the total catalyst weight. A sulfur content of 0.005 to 0.1% is preferred.

It should be noted that U.S. Pat. No. 3,076,810, discloses a sodium-promoted palladium catalyst. Patentees characterize sulfur as deleterious, reducing activity and product selectivity.

THE HYDROGENATION REACTION

Typical hydrogenation reactions take place using the inventive catalysts at temperatures of 125° to 275° C. preferably 150°-205° C. and at hydrogen pressures of 0 to 250 psig preferably 0-75 psig.

The reaction takes place in a conventional reaction apparatus, such as a stirred autoclave for batch hydrogenations and a trickle bed reactor for continuous hydrogenation runs.

In the continuous process the feed (including diluent, if any) is charged to the reaction zone at 0.1-10.0 preferably 0.1-5 liquid hourly space velocity (LHSV).

The feed can be charged in admixture with up to about 95 vol. % of an inert diluent. The diluent can be selected from saturated hydrocarbons, aromatic hydrocarbons, ethers, alcohols or a reaction product expected from the hydrogenation reaction, e.g. cyclohexanol from complete phenol hydrogenation. If aromatic hydrocarbons are employed they should be difficult or nonreducible under the hydrogenation conditions employed. Examples of suitable diluents include cyclohexanol, ortho-xylene, diethylene glycol dibutyl ether, 1-octanol and decane.

REGENERATION

Conventional techniques for rejuvenating or regenerating the catalyst for further use are operable. One preferred method comprises the steps of (1) heating the used catalyst in air for controlled carbon burnoff, and (2) contacting the catalyst with hydrogen under conditions to reduce the oxidized palladium. Operable parameters for the heating and hydrogen-contacting steps are 350°-500° C. and 1-6 hours.

Other conventional catalyst treatment and/or rejuvenation methods can be used in combination with the procedures discussed herein.

EXAMPLES

Example I

The hydrogenation of phenol to cyclohexanone using a 70/30 phenol/cyclohexanone mixture as feed in a continuous flow trickle bed reactor was studied. The base catalyst was a palladium on alumina catalyst. It was modified by sequential additions of sodium carbonate, sodium sulfide, and thioanisole. The results attained using the catalyst at various stages in its production are given in Table I.

Except as noted, the hydrogen flow rate was 0.32 L/minute in the hydrogenation runs.

TABLE I

| Run No. | Catalyst | Reaction Temp. °C. | Hydrogen Pressure, psig. | LHSV | Wt. % Phenol Conversion | Selectivity Wt. % | |
|---|---|---|---|---|---|---|---|
| | | | | | | Cyclohexanone | Cyclohexanol |
| 1 | 0.5% Pd/Al$_2$O$_3$ | 188 | 70 | 0.4 | 54 | 20 | 77 |
| 2 | 0.5% Pd/Al$_2$O$_3$ 6.0% Na$_2$CO$_3$ | 185 | 15 | 0.5 | 88 | 85 | 14 |
| 3 | 0.5% Pd/Al$_2$O$_3$ 6.0% Na$_2$CO$_3$ 0.0125% S* | 182 | 15 | 0.5 | 97 | 63 | 37 |
| 4 | 0.5% Pd/Al$_2$O$_3$ 6.0% Na$_2$CO$_3$ 0.05% S** | 178 | 15 | 0.8 | 60 | 87 | 13 |

*sulfur from Na$_2$S added by impregnation of catalyst
**sulfur from Na$_2$S and thioanisole added with feed Table I demonstrates the superiority of the catalyst of the invention over comparable catalysts, which do not contain sulfur. Note in Runs 3 and 4, which employed the applicant's catalyst, lower reaction temperatures and hydrogen pressures were used, while good to excellent phenol conversion and cyclohexanone selectivity resulted.

Example II

The catalyst produced in Example I, Run 4 was treated with air at 180°-233° C. for 2.0 hours, then reduced with hydrogen for 8.0 hours at 212° C. After use in Runs 5 and 6 the catalyst was regenerated by heating in air at 400° C. for 4.5 hours and then reduced with hydrogen at 400° C. for 3.5 hours.

Table II shows the results obtained using these catalysts.

TABLE II

| Run No. | Catalyst | Reaction Temp., °C. | H$_2$ Press., psig. | LHSV, v/v/hr | Wt. % PhOH Conv. | Selectivity, Wt. % | |
|---|---|---|---|---|---|---|---|
| | | | | | | Cyclo-hexanone | Cyclo-hexanol |
| 5 | Air-treated | 176 | 15 | 0.6 | 96 | 89 | 11 |
| 6(a) | Air-treated | 185 | 15 | 0.6 | 97 | 94 | 5 |
| 7(a) | Regenerated | 199 | 15 | 0.75 | 96 | 91 | 8 |

(a)Hydrogen flow rate of 0.24 L/minute

This table shows the outstanding results in terms of phenol conversion and cyclohexanone selectivity obtained when the sulfided catalyst of this invention is subjected to the highly preferred heat treatment in the presence of air and then hydrogen.

Example III

In this example the performance of the catalyst of Example II, Run 6 was compared to a catalyst produced in accordance with Example 6 of U.S. Pat. No. 3,076,810. Reaction parameters and results are given in Table III.

TABLE III

|  | Reaction Conditions | | | |
|---|---|---|---|---|
|  | Temp. °C. | Pressure psig | Residence time/ min. | Selectivity to Cyclohexane |
| Catalyst of Invention (17 g/hr phenol feed) | 180–185 | 15 | 48 | 95% |
| Catalyst, U.S. Pat. No. 3,076,810* Example 6 | 185–195 | 135–145 | 540 | 96% |

*5% Pd/Carbon, 10,000 g/hr phenol feed, 10–15 g/hr catalyst feed, 0.1 g/hr $Na_2CO_3$ feed As Table III demonstrates, applicant's catalyst is superior in activity, requiring only 15 psig pressure and 48 min residence time, compared too patentees' 135 psig pressure and 9 hour residence time.

Reasonable variations, such as would occur to a skilled artisan, may be made herein without departing from the scope of the invention.

I claim:

1. A process for the preparation of a hydrogenation catalyst consisting essentially of the steps of:
   (1) contacting an inert support with a Group VIII metal substance chosen from nickel, platinum, and palladium,
   (2) contacting the metal-containing support of (1) with an alkali metal promoter to form a catalyst composite,
   (3) treating the composite with a compound of divalent sulfur, and
   (4) heating the sulfided composite at an elevated temperature in the presence of an oxidizing gas and subsequently in the presence of a reducing gas to produce an active catalyst effective for the hydrogenation of unsaturated compounds.

2. A process according to claim 1 wherein, based on total catalyst weight, the catalyst contains between 0.01–5 weight percent Group VIII metal, between 0.1–5 weight percent alkali metal, and between 0.001–1 weight percent sulfur.

3. A process according to claim 1 wherein the heating is conducted at temperature of 150°–250° C.

4. A process of claim 1 wherein steps (2) and (3) occur simultaneously.

5. A process according to claim 1 in which step (3) is carried out in a two-stage sequence comprising:
   (a) contacting the product of step (2) with sodium sulfide, and
   (b) contacting the product of step (a) with a solution of thioanisole.

6. A process according to claim 2 wherein said alkali metal is sodium, and said divalent sulfur compound is selected from the group consisting or organic sulfides, disulfides, thioacids, and mercaptans, and inorganic sulfides and hydro sulfides.

7. A process according to claim 6 wherein Group VIII metal is palladium, support is alumina, and divalent sulfur compound is thioanisole.

8. A process according to claim 6 wherein said heating is effected with air followed by hydrogen at a temperature of 150°–250° C.

9. A process according to claim 2 wherein the alkali metal promoted composite is first sulfided by treating with sodium sulfide and then subsequently with thioanisole.

10. A process according to claim 9 wherein said Group VIII metal is palladium, said alkali metal is sodium, and said support is alumina.

* * * * *

UNITED STATES PATENT AND TRADEMARK OFFICE
CERTIFICATE OF CORRECTION

PATENT NO. : 4,520,129

DATED : May 28, 1985

INVENTOR(S) : Timothy P. Murtha

It is certified that error appears in the above-identified patent and that said Letters Patent is hereby corrected as shown below:

On the title page;

Assignee should be: Phillips Petroleum Company
Bartlesville, Oklahoma

Signed and Sealed this

Third Day of September 1985

[SEAL]

*Attest:*

DONALD J. QUIGG

*Attesting Officer*   Acting Commissioner of Patents and Trademarks - Designate